United States Patent
Ice

(10) Patent No.: US 7,717,266 B2
(45) Date of Patent: May 18, 2010

(54) COMPACT, ROLLED PACKAGING FOR A GROUP OF SANITARY ITEMS

(76) Inventor: Lisa Ice, 505 Winems Ct. SE., Albuquerque, NM (US) 87123

(*) Notice: Subject to any disclaimer, the term of this patent is extended or adjusted under 35 U.S.C. 154(b) by 735 days.

(21) Appl. No.: 11/306,893

(22) Filed: Jan. 15, 2006

(65) Prior Publication Data
US 2007/0163909 A1 Jul. 19, 2007

(51) Int. Cl.
B65D 69/00 (2006.01)
B65D 71/00 (2006.01)

(52) U.S. Cl. .................. 206/440; 206/223; 206/226; 206/397; 206/410; 206/225

(58) Field of Classification Search ............ 206/440, 206/210, 223, 225, 226, 410, 494, 524.8, 206/397, 398, 812; 604/385.02
See application file for complete search history.

(56) References Cited

U.S. PATENT DOCUMENTS

| | | | |
|---|---|---|---|
| 1,025,207 A | 5/1912 | Sanford | |
| 2,130,728 A * | 9/1938 | Berkman | 206/226 |
| 2,814,382 A * | 11/1957 | Lassiter | 53/408 |
| 3,061,170 A * | 10/1962 | Baker | 383/109 |
| 3,437,195 A * | 4/1969 | Hill | 206/226 |
| 3,770,118 A | 11/1973 | Jones | 206/47 |
| 3,892,310 A * | 7/1975 | Welin-Berger | 206/210 |
| 4,221,221 A | 9/1980 | Ehrlich | 128/284 |
| 4,387,832 A * | 6/1983 | Margulies | 221/63 |
| 4,702,378 A | 10/1987 | Finkel | 206/581 |
| 4,738,678 A | 4/1988 | Paulis | 604/385 |
| 4,743,240 A | 5/1988 | Powell | 604/385 |
| 4,753,647 A | 6/1988 | Curtis | 604/385 |
| 4,790,840 A | 12/1988 | Cortina | 604/385.1 |
| 4,808,175 A | 2/1989 | Hansen | 604/385.1 |
| 4,917,693 A | 4/1990 | Terry | 604/385.1 |
| 4,931,052 A | 6/1990 | Feldman | 604/385.1 |
| 4,964,859 A | 10/1990 | Feldman | 604/385.1 |
| 5,071,414 A | 12/1991 | Elliott | 604/385.1 |
| 5,304,158 A | 4/1994 | Webb | 604/385.1 |
| 5,443,161 A | 8/1995 | Jonese | 206/581 |
| 5,569,230 A | 10/1996 | Fisher | 604/385.1 |
| 5,575,784 A | 11/1996 | Ames-Ooten | 604/385.1 |
| 5,582,605 A | 12/1996 | Lepie | 604/385.1 |
| 5,702,379 A | 12/1997 | Preiss | 604/385.1 |
| 5,706,950 A | 1/1998 | Houghton | 206/581 |
| 5,816,709 A | 10/1998 | Demus | 383/61 |
| 5,827,251 A | 10/1998 | Moder | 604/385 |
| 5,891,127 A | 4/1999 | Moder | 604/385 |
| 5,964,741 A | 10/1999 | Moder | 604/385 |

(Continued)

Primary Examiner—David T. Fidei
Assistant Examiner—Chun Cheung

(57) ABSTRACT

A packaging method for sanitary items, the preferred embodiment of which is a diapering kit. In the diapering kit example, one or more diaper wipe(s) (12) are rolled around a disposal bag (10). The disposal bag folds back over the wipes, and a diaper (20) is rolled around it. The disposal bag is closed by a releasable closure (18), leaving the closed end of the disposal bag exposed, and folds back over the rolled diaper. A third reusable closure (22) closes the disposal bag at the other end of the rolled diaper, and the disposal bag folds back over the rolled diaper to the half-way point where it is closed tightly around the rolled diaper by a fourth releasable closure (32). Four additional item storage locations are created within the disposal bag, with potential for storing several different material types.

15 Claims, 3 Drawing Sheets

U.S. PATENT DOCUMENTS

| | | | |
|---|---|---|---|
| 5,986,165 A * | 11/1999 | Moder et al. | 604/358 |
| 6,004,307 A | 12/1999 | Colon | 604/385.1 |
| 6,380,455 B1 | 4/2002 | Moder | 604/385 |
| D474,680 S | 5/2003 | Ling | D9/305 |
| 6,601,706 B2 | 8/2003 | McManus | 206/526 |
| 6,723,080 B1 | 4/2004 | Habib | 604/385.06 |
| 7,150,354 B2 * | 12/2006 | Snell | 206/223 |
| 7,168,561 B2 * | 1/2007 | Dufresne | 206/410 |
| 2002/0065500 A1 | 5/2002 | Rossi | 604/385.06 |
| 2002/0156448 A1 | 10/2002 | Steger | 604/385.06 |
| 2003/0109841 A1 | 6/2003 | Edwards | 604/385.06 |
| 2004/0092901 A1 | 5/2004 | Reece | 604/385.06 |
| 2005/0138894 A1 | 6/2005 | Snell | 53/412 |
| 2005/0143704 A1 | 6/2005 | Snell | 604/385.06 |
| 2005/0143706 A1 | 6/2005 | Snell | 604/385.06 |
| 2005/0173292 A1 | 8/2005 | Klose | 206/581 |
| 2005/0203476 A1 | 9/2005 | Stegall | 604/385.06 |
| 2005/0205456 A1 * | 9/2005 | Meyer et al. | 206/525 |
| 2005/0261655 A1 | 11/2005 | Nijs | 604/385.06 |

* cited by examiner

COMPACT, ROLLED PACKAGING FOR A GROUP OF SANITARY ITEMS

BACKGROUND OF THE INVENTION

1. Field of Invention

The invention relates to compact packaging methods for a plurality of related items, specifically those with storage means in the core; for example, a sanitary kit such as a disposable diaper changing kit including diapering items such as a diaper, a diaper wipe, and a impermeable disposal bag.

2. Prior Art

Many sanitary tasks such as changing a diaper require a number of items. In order to increase convenience, the concept of such products as a disposable diaper changing kit has evolved in which disposable versions of these required items are carried in a single, throwaway package. At a minimum, the example of a diapering kit requires a disposable diaper and one or more diaper wipes. In addition, most such kits include an impermeable bag for sanitary disposal. Additional items can include a barrier material for use as a changing surface and packages of baby powder, diaper rash cream, etc.

Previous patents (U.S. Pat. No. 4,702,378 to Finkel, et. al. on Oct. 27, 1987; U.S. Pat. No. 5,443,161 to Jonese on Aug. 22, 1995; and U.S. Pat. No. 6,723,080 B1 to Habib, et. al. on Apr. 20, 2004) have attempted to address the need for making such kits smaller in size, resistant to water, disposable, and even capable of being dispensed from a vending machine. However, a more compact and simpler arrangement with fewer packaging elements that addressed these needs would be even more convenient. The invention disclosed herein possesses all of these properties.

Another approach to making the carrying of diaper changing supplies more convenient is to modify the diaper to carry additional items. U.S. Pat. No. 4,221,221 to Ehrlich on Sep. 9, 1980; U.S. Pat. No. 4,931,052 to Feldman on Jun. 5, 1990; and 5,582,605 to Lepie on Dec. 10, 1996 take this approach. These inventions do not address the need for a more compact form of the kit or the need for water resistance. In addition, they require the addition of many packaging elements, all of which must be worn along with the diaper and therefore be hardy enough to stay together in a wide variety of situations. U.S. Pat. No. 6,004,307 to Colon, et. al, on Dec. 21, 1999 combines this strategy with an exterior water impermeable cover member and a more compact, folded arrangement. This invention also suffers from the need for several complicated packaging elements to be worn by the diaper wearer as well as not being as compact as the invention disclosed herein.

The general need for compact packaging has led to a number of inventions in which the core of a rolled object has been used for storing related materials. Such patents, including U.S. Pat. No. 2,130,728 to Berkman on Sep. 20, 1938, usually use caps placed on the ends of a hard, hollow core to keep the related materials inside the rolled object. Such concepts require additional packaging material that must be produced and disposed. A packaging concept, U.S. Pat. No. 3,437,195, patented to Hill on Aug. 24, 1967, uses multiple impermeable, flexible membranes to store film materials in hermetically sealed packages, internal to one another. The invention disclosed herein will use only a single impermeable, flexible membrane, which is also a functional element within the kit. U.S. Pat. No. 5,569,230 to Fisher on Oct. 29, 1996, for an individually packaged sanitary napkin with a cleaning wipe, allows for fairly compact packaging of a sanitary napkin within a material that can be used for disposal. This patent requires the creation of a pouch as part of the wrapper and within which the cleaning wipe or sanitary napkin may be disposed. It does not possess the concept of using an unmodified disposal bag as the primary means of packaging. In addition, the sanitary wrap is in a C-fold, as opposed to the more compact rolled arrangement. The patent is also specific to packaging a sanitary napkin with an adhesive backing, and does not address the broader field of sanitary item packaging such as a diapering kit and the potential need for packaging additional kit items other than a cleansing wipe. All of these packaging concepts also suffer from difficulty associated with removing the items from the packaging material, a difficulty that is eased by this invention.

BACKGROUND OF INVENTION

Objects and Advantages

Accordingly, several objects and advantages of my invention are packaging of a sanitary kit that it is:
(1) extremely compact;
(2) water and wear resistant;
(3) simple, requiring materials that are functional elements in such a kit and a few releasable closures;
(4) in a conformation that can be vended; and
(5) easily opened for use. A further object and advantage is to provide packaging for groups of sanitary items that is convenient and can incorporate additional kit items, if they are beneficial.

Further objects and advantages of my invention will become apparent from a consideration of drawings and ensuing description.

SUMMARY

In accordance with the present invention, the compact, rolled packaging for sanitary items includes, at a minimum, a primary sanitary item such as a diaper, one or more cleansing wipes, and a useful flexible membrane, such as a disposal bag, in a single package. The preferred embodiment is a diapering kit. In the preferred embodiment, diaper wipes are disposed within the disposal bag inside the rolled core of the diaper. The disposal bag folds tightly back over the diaper twice at releasable closures and is closed around the rolled diaper to maintain the diaper's rolled conformation and protect the diapering kit from water and wear. Additional folds in the disposal bag within the diaper's core allow for easy access to the diaper wipes. In addition, multiple convenient locations are created for adding beneficial diapering kit elements, with a multitude of physical characteristics.

DRAWINGS

Figures

DRAWINGS

Figure 1:
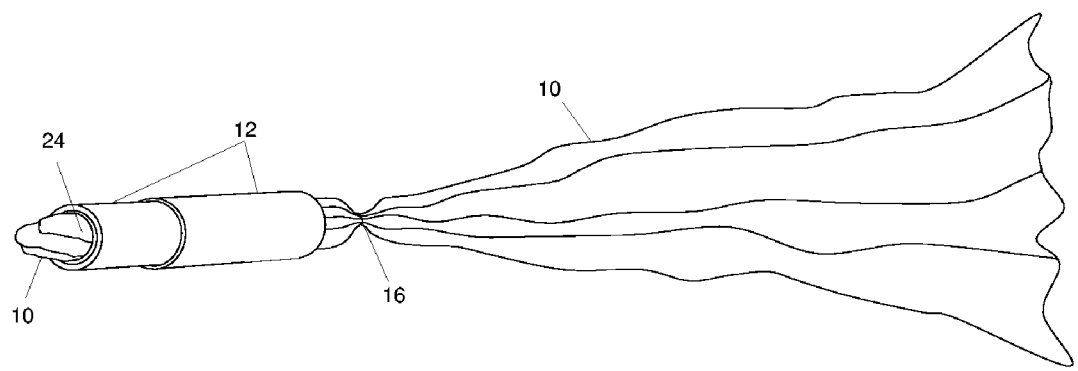
FIG. 1 shows rolled wipes and a disposal bag in an initial configuration prior to folding the disposal bag for the first time.

References Numerals 10 disposal bag
12 rolled wipes
16 first releasable closure
18 second releasable closure
20 rolled diaper
22 third releasable closure
24 first item storage location
26 second item storage location
28 third item storage location
30 fourth item storage location
32 fourth releasable closure
34 release attachment for third releasable closure

DETAILED DESCRIPTION

Preferred Embodiment—FIGS. 1, 2, 3, 4

FIG. 1 shows an early configuration of the diapering kit package embodiment. A disposal bag 10 is collapsed such that it is compact horizontally, but extends its full length longitudinally. About two centimeters from the end of the disposal bag, one or more folded wipes(s) are rolled around the bag, forming rolled wipe(s) 12. In my preferred method, a first releasable closure 16 closes the bag within two centimeters of the rolled wipe(s). The interior of disposal bag 10, from the end of the disposal bag to the first releasable closure 16, creates a first item storage location 24. This location is especially ideal for any non-solid items, such as diaper rash cream. The first releasable closure 16 can be a twist in disposal bag 10, a plastic string, or any other easily releasable closure. The rolled wipe(s) are positioned such that the length from the end of disposal bag 10 to releasable closure 16 is less than the width of the diaper to be included in the diapering kit.

Figure 2:
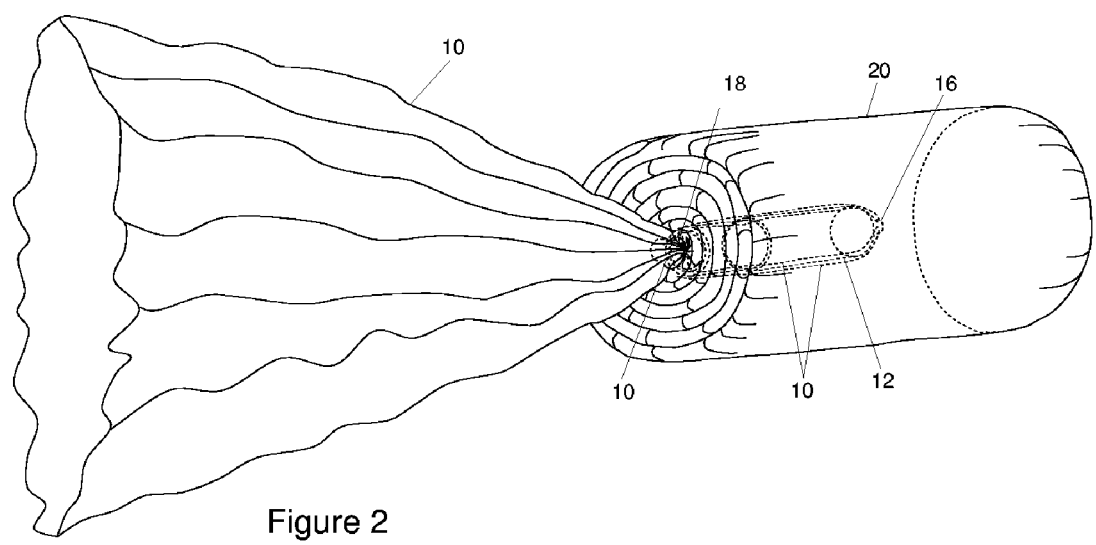
FIG. 2 shows a diaper rolled around the disposal bag which has been folded over the rolled wipes.

FIG. 2 shows a later stage in the packaging of the diapering kit. Disposal bag 10 has been folded back over at first releasable closure 16 and positioned tightly against the rolled wipe(s) 12. A diaper has been rolled tightly around rolled wipe(s) 12 within folded disposal bag 10. The rolled diaper thereby becomes rolled diaper 20. If desired, before rolling the diaper around the bag-enfolded wipe(s), items with a dry exterior, such as prepackaged creams or barrier material for use as a diapering surface, can be placed between disposal bag 10 and rolled diaper 20. This area forms a second item storage location 26. A second releasable closure 18 closes the disposal bag 10 immediately adjacent to where it protrudes from rolled diaper 20. Releasable closure 18 thus completely encloses the rolled wipe(s) 12 within disposal bag 10. My presently preferred material for the second releasable closure 18 is a breakable plastic string, although other methods, such as twisting disposal bag 10, could be used.

Figure 3:
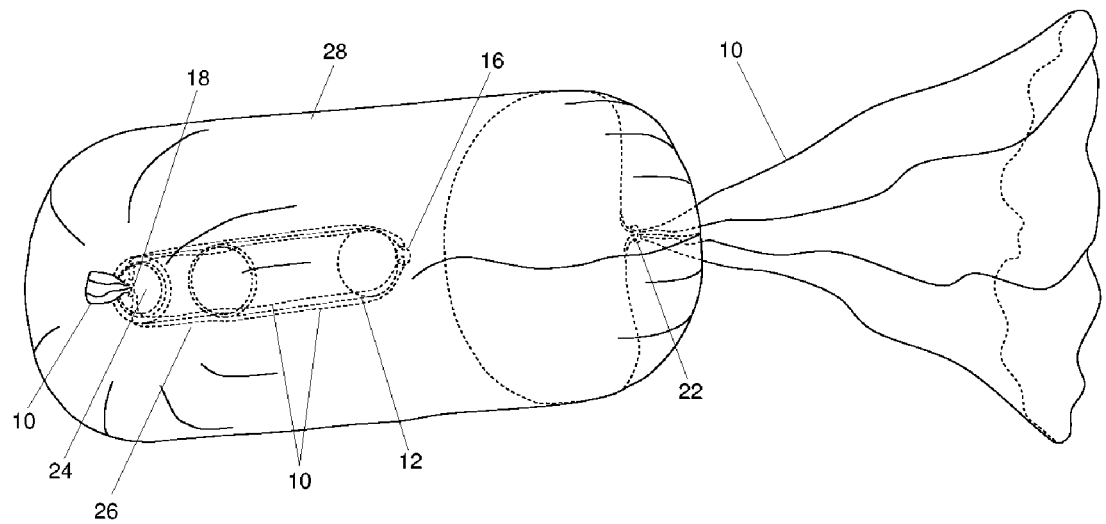
FIG. 3 shows the disposal bag folded back over the rolled diaper and closed prior to its final fold and closure.

FIG. 3 shows the diapering kit just prior to completion. At releasable closure 18, disposal bag 10 has been tightly folded back over the rolled diaper and has been closed by a third releasable closure 22. A third item storage location 28 is thereby formed between the exterior of rolled diaper 20 and the interior of disposal bag 10. My current preference is that releasable closure 22 be one that can easily open by using a release attachment 34. Plastic string could be used as the material for both releasable closure 22 and release attachment 34, such that pulling on release attachment 34 breaks releasable closure 22. The end of disposal bag 10 is still exposed, and rolled diaper 20 and rolled wipe(s) 12 are contained within the disposal bag in a manner that protects the entire kit from water and wear.

Figure 4:
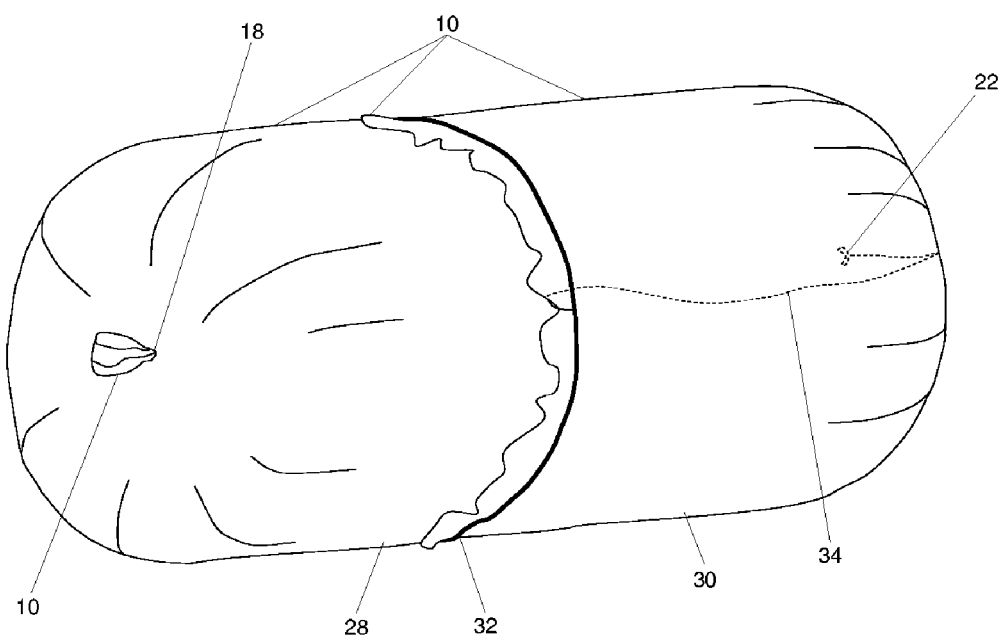
FIG. 4 shows a completed diapering kit packaged as disclosed in this invention.

FIG. 4 shows the diapering kit completely packaged as disclosed in my invention. Disposal bag 10 has been folded back over at releasable closure 22 such that it ends slightly past the midpoint of rolled diaper 20. Fourth releasable closure 32 holds disposal bag 10 tightly against itself, forming a fourth storage location 30 between two portions of disposal bag 10. Fourth storage location 30 is ideal for items that are needed early in the diapering process, such as an impermeable barrier for use as a changing surface. In addition, the placement of releasable closure 32 at approximately the midpoint of enclosed rolled diaper 20 holds the diaper in its most compactly-rolled conformation. My current preference is that releasable closure 32 be one that can be reused to close disposal bag 10 again around a soiled diaper and diaper wipe(s), such as a twistable wire.

OPERATION

Preferred Embodiment—FIGS. 1, 2, 3, 4, 5

Opening the diapering kit packaging in order to use the items contained within is intentionally simple.

Figure 5:
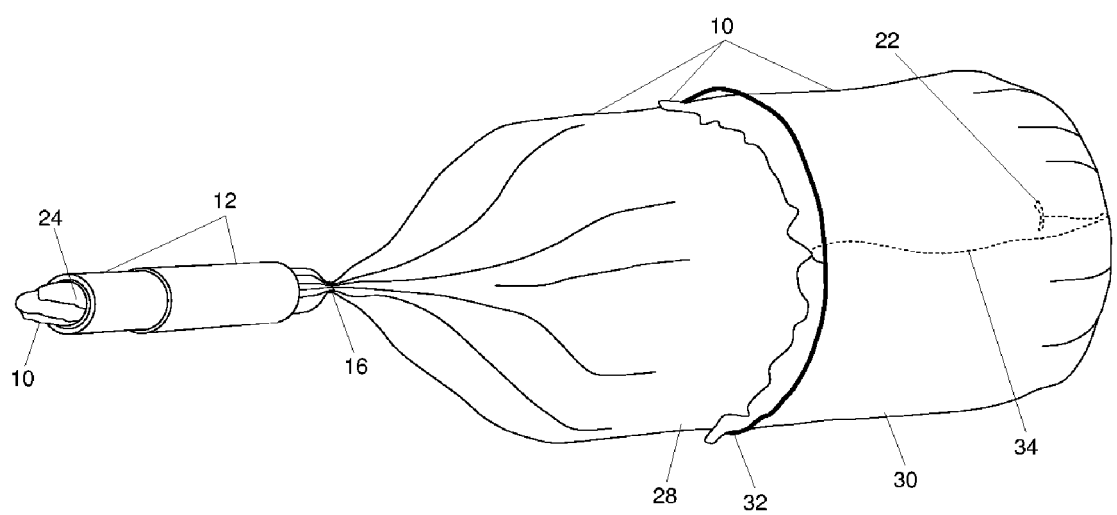
FIG. 5 shows a diapering kit that has had the final two closures opened and the rolled diaper loosened, with the diaper wipe(s) ready for use.

First, one opens releasable closure 32 and pulls on release attachment 34 to open releasable closure 22. These actions provide access to storage location 30 and loosen the rolled diaper from around the rolled wipe(s) within storage bag 10. Next, one pulls on the end of disposal bag 10, causing second releasable closure 18 to open. As shown in FIG. 5, disposal bag 10 extends to its full length, with a compact conformation in the horizontal direction toward the end of the bag, but retaining the now loosely rolled diaper. Rolled wipe(s) 12 are thereby exposed for removal from around the disposal bag 10 and subsequent use.

After using the diaper wipe(s), one can access the clean rolled diaper, which was made easily accessible when releasable closure 22 was opened. Rolled diaper 20 is now in an even looser conformation within disposal bag 10 due to the removal of the items around which it was rolled. It can be removed from disposal bag 10 and unrolled for use. Any items in second or third item storage locations 26 and 28 can also be removed from storage easily at this time. An item in first item storage location 24 can be removed from storage after removing rolled diaper 20 and releasing first releasable closure 16.

After removing the clean rolled diaper and any items in one of the four item storage locations from the disposal bag, soiled items, including the soiled diaper and soiled diaper wipe(s), are placed inside disposal bag 10. If the first item storage location is not used, first releasable closure 16 will release with the weight of the soiled diaper, to allow access to the full capacity of the disposal bag. The fourth releasable closure is reusable, allowing one to then seal the disposal bag 10. The soiled diaper and used wipes are thereby contained for convenient, sanitary disposal.

CONCLUSION, RAMIFICATIONS, AND SCOPE

The reader will see that, according to the invention, I have provided an easy-to-use, extremely compact, and convenient method for packaging a kit containing all essential items of a sanitary kit such as that for changing a diaper.

While the above description contains many specificities, these should not be construed as limitations on the scope of the invention, but as exemplifications of the presently preferred embodiment thereof. Many other ramifications and variations are possible within the teachings of the invention. For example:

First releasable closure 16 could be eliminated, with disposal bag 10 simply folding back over diaper wipe(s) at approximately the same location.

Both first releasable closure 16 and the associated first fold of disposal bag 10 could be removed entirely, making second releasable closure 18 and its associated fold the first releasable closure and associated fold. This form increases the simplicity of the invention, but reduces accessibility of the diaper wipes(s).

Fourth releasable closure 32, the final fold of disposal bag 10, and release attachment 34 could all be removed. This form increases the simplicity of the invention, but reduces accessibility to rolled diaper 20, does not preserve the compact conformation of the packaging as well, and eliminates fourth storage item location 30.

The disposal bag could be modified to form a barrier material for use as a changing surface.

Other additions and modifications to the packaging could be made that would reduce the simplicity, but enhance ease of use.

Other embodiments containing other items for storage could be created.

Air can be removed from the packaged kit to compact it further.

In addition, the type of sanitary kit could be quite different from the preferred embodiment, including such items as sanitary napkins and cleansing wipes instead of diapers and diaper wipes.

Thus the scope of the invention should be determined by the appended claims and their legal equivalents, and not by the example given.

What is claimed is:

1. A form of packaging a group of related items into a kit, comprising:
    (a) a rolled item requiring packaging, with a core at said rolled item's center
    (b) a second item requiring packaging with a conformation allowing placement within the core of said rolled item
    (c) a flexible membrane requiring packaging
    (d) a first membrane closure that is releasable without damaging said flexible membrane
    (e) a second membrane closure that is releasable without damaging said flexible membrane
    (f) said first membrane closure holding said flexible membrane around said second item to form an enclosing portion of said flexible membrane
    (g) said rolled item's core containing said second item and said enclosing portion of said flexible membrane such that said enclosing portion of said flexible membrane separates said second item from interior of said rolled item
    (h) said flexible membrane folding at said first membrane closure
    (i) said flexible membrane containing said rolled item between said first membrane closure and said second membrane closure
    (j) said flexible membrane and said first and second membrane closures holding said rolled item in a rolled conformation around said second item whereby two items and a flexible membrane are packaged simply and compactly into a kit using only kit elements and two releasable closures.

2. The form of packaging of claim 1 wherein said rolled item and said second item requiring packaging are sanitary items.

3. The form of packaging of claim 2 wherein said second sanitary item is a wet cleansing cloth and said flexible membrane is impermeable to liquids.

4. The form of packaging of claim 1 wherein said second item possesses properties damaging to said rolled item and said flexible membrane is impermeable to said damaging properties, whereby said flexible membrane provides protection to said rolled item from the properties of said second item.

5. The form of packaging of claim 1 wherein said rolled item requiring packaging is a diaper, said second item requiring packaging is at least one diaper wipe, and said flexible membrane is moisture impermeable disposal bag or diapering surface.

6. The form of packaging of claim 1 wherein said rolled item requiring packaging is a sanitary napkin.

7. The form of packaging of claim 6 wherein said second item requiring packaging is a tampon.

8. The form of packaging of claim 1 wherein said first membrane closure is a twist in said flexible membrane.

9. The form of packaging of claim 1 wherein said first membrane closure is a flexible plastic element.

10. The form of packaging of claim 1 wherein an additional item is packaged between said rolled item and said flexible membrane, exterior to said rolled item, proximal to said first membrane closure and said second membrane closure.

11. The form of packaging of claim 1 wherein an additional item is packaged between said flexible membrane, enclosing said second item, and said rolled item, interior to said rolled item, proximal to said first membrane closure.

12. The form of packaging of claim 1 wherein said flexible membrane possesses at least one fold interior to said rolled item.

13. The form of packaging of claim 12 wherein said second item is packaged between folds of said flexible membrane and an additional item is packaged in the core of the folded flexible membrane.

14. The form of packaging of claim 1 wherein an additional membrane closure that is releasable without damaging said flexible membrane exists around the circumference of said rolled item.

15. The form of packaging of claim 1 wherein said rolled item possesses properties damaging to said second item and said flexible membrane is impermeable to said damaging properties, whereby said flexible membrane provides protection to said second item from the properties of said rolled item.

* * * * *